United States Patent [19]

Itakura et al.

[11] Patent Number: 5,750,380
[45] Date of Patent: May 12, 1998

[54] DNA POLYMERASE MEDIATED SYNTHESIS OF DOUBLE STRANDED NUCLEIC ACIDS

[75] Inventors: Keiichi Itakura, Arcadia; John J. Rossi, Azusa, both of Calif.

[73] Assignee: City of Hope Research Institute, Duarte, Calif.

[21] Appl. No.: 425,215

[22] Filed: Apr. 18, 1995

Related U.S. Application Data

[60] Continuation of Ser. No. 135,066, Dec. 18, 1987, abandoned, which is a division of Ser. No. 943,890, Dec. 18, 1986, abandoned, which is a continuation of Ser. No. 558,905, Dec. 7, 1983, abandoned, which is a continuation of Ser. No. 279,166, Jun. 30, 1981, abandoned.

[51] Int. Cl.$^6$ ................................................. C12P 19/34
[52] U.S. Cl. ........................ 435/91.1; 435/91.2; 435/91.5; 536/22.1; 536/23.1; 536/24.3; 536/24.31; 536/24.32; 536/24.33; 536/25.3; 935/77; 935/78
[58] Field of Search ........................... 536/22.1, 23.1, 536/24.1, 24.3–24.33, 25.3; 935/77, 78; 435/91.1, 91.2, 91.5

[56] References Cited

PUBLICATIONS

Kleppe et. al., Studies on Polynucleotides, Journal of Mol. Biol. 1971, 56, 341–361.
Wu, et al., *J. Mol. Biol.* (1968) 35:523–527, "Structure and Base Sequence in the Cohesive Ends of Bacteriophage Lambda DNA".
Wu, et al., *J. Mol. Biol.* (1971) 57:491–511, "Nucleotide Sequence Analysis of DNA".
Wu, R., *J. Mol. Biol.* (1970 51:501–521, "Nucleotide Sequence Analysis of DNA".
Padmanabhan, et al. *J. Mol. Biol.* (1972) 69:201–207, "Arrangement of DNA in Lambda Bacteriophage Heads".
Padmanabhan, et al., *J. Mol. Biol.* (1972) 65:447–467, "Nucleotide Sequence Analysis of DNA".
Padmanabhan, et la., *J. Mol. Biol.* (1973) 75:741–744, "Nucleotide Sequence Analaysis of DNA".
Ghangas, et al., *J. Biol. Chemistry* (1985) 250:4601–4606, "Specific Hydrolysis of the Cohesive Ends of Bacteriophage Lambda DNA by Three Single Stand–Specific Nucleases".
Betz et al. (1981) Gene, vol. 13, pp. 1–12.
Old et al. (1975) J. Mol. Biol., vol. 92, pp. 331–339.
Roberts (1980) Nucleic Acids Research, vol. 8, No. 1, pp. r63–r80.
Maniatis et al. *Molecular Cloning, A Laboratory Manual* (Cold Spring Harbor Labs, Cold Spring Harbor, NY, 1982) pp. 98–101.
Bethesda Research Labs. Catalogue (Life Technologies Inc., Gaithersburg, MD., 1985) p. 9.
Hudson et al. (1981) Endocrinology, vol. 108, pp. 353–356.
O'Farrell et al, Molec. gen. Genet. 179:421–435, "A Restriction Map of the Bacteriophage T4 Genome" Sep. 1980.
Rigby et al, J. Mol. Biol., 113:237–251, "Labeling Deoxyribonucleic Acid to High Specific Activity in Vitro by Nick Translation with DNA Polymerase I" (1977).
*Gene Expression*, Lewin, vol. 3, John Wiley & Sons, New York, 330, 331, 337, 621, 622 (1977).
Kornberg, *DNA Replication*, W. H. Freeman and Company, San Francisco, 90–93 (1980).

*Primary Examiner*—Ardin H. Marschel
*Attorney, Agent, or Firm*—Rothwell, Figg, Ernst & Kurz

[57] ABSTRACT

A first polynucleotide is formed with a first particular sequence of nucleotides such as by providing a solid-phase support and adding nucleotides to the support. A second polynucleotide is formed in a similar manner with a second particular sequence of nucleotides which are complementary to the nucleotides in the first polynucleotide at first particular ends of the polynucleotides. The first particular ends may be the 3'-ends of the polynucleotides. The polynucleotides are hybridized or annealed at their 3'-ends to form a base-pair complementary stretch between the first and second polynucleotides. A repair synthesis is then provided in the first and second polynucleotides at second ends (such as the 5'-ends) opposite the first particular ends to provide a double-stranded polynucleotide. The repair synthesis may be monitored by labelling the second end (or 5'-end) of one or both of the nucleotides with radioactivity and then subjecting the nucleotides to an enzymatic reaction.

2 Claims, 10 Drawing Sheets

| STEP | SOLVENT OR REAGENT | AMOUNT | SHAKING TIME | NUMBER OF OPERATIONS |
|---|---|---|---|---|
| 1 | PYRIDINE | 10ml | 1 | 2 |
| 2 | 10% SOLUTION $(CH_3CO)_2O$ IN PYRIDINE | 10ml | 60 | 1 |
| 3 | PYRIDINE | 10ml | 1 | 2 |
| 4 | $CHCl_3$–MeOH (7:3v/v) | 10ml | 1 | 3 |
| 5 | 2% BSA | 10ml | 0.5 | 2 |
| 6 | $CHCl_3$–MeOH (7:3v/v) | 10ml | 1 | 2 |
| 7 | PYRIDINE | 10ml | 1 | 2 |
| 8 | DIMER OR TRIMER IN PYRIDINE | 5 EQUIVALENT | CO-EVAPORATION | 1 |
| 9 | TPSTα IN PRYIDINE | 10 EQUIVALENT /5ml | 120 | 1 |

FIG.3

DNA POLYMERASE MEDIATED SYNTHESIS OF DOUBLE STRANDED NUCLEIC ACIDS

This is a continuation of application Ser. No. 135,066 which is a division of application Ser. No. 943,890 filed Dec. 18, 1986, abandoned, which in turn is a continuation of application Ser. No. 558,905 filed Dec. 7, 1983, abandoned, which in turn is a continuation of application Ser. No. 279,166 filed Jun. 30, 1981, now abandoned.

This invention relates to methods of producing DNA and particularly to methods of producing double-stranded DNA. The invention especially relates to methods of producing DNA having relatively long sequences of nucleotides.

In recent years, DNA fragments have been produced for various purposes. For example, these fragments have been produced for the purpose of synthesizing medicines for use by humans and animals. Work is also proceeding in synthesizing DNA, and fragments of DNA, for use in a number of other fields including agriculture.

The methods used thus far to produce fragments of DNA have been relatively laborious and inefficient. For example, DNA fragments have been produced by the ligation of single-stranded fragments aligned by complementary overlaps. This method has been used primarily to synthesize DNA fragments each of which has a maximum length in the order of twenty (20) nucleotides. However, the synthesis of eighty two (82) nucleotides would have to be provided in order to produce, by this method, a base pair fragment having a length of forty two (42) nucleotides.

Various attempts have been made to synthesize DNA fragments each of which has a length longer than twenty (20) nucleotides. These attempts have not been successful. In spite of such attempts, the synthesis of DNA fragments, particularly of long length, is still laborious and inefficient.

This invention provides a satisfactory method of synthesizing DNA fragments, particularly DNA fragments having a relatively long length. For example, a 42-base-pair DNA fragment comprising an E.Coli "putative promoter" has been produced by the method constituting this invention.

In the method constituting this invention, a first polynucleotide is formed with a first particular sequence of nucleotides such as by providing a solid-phase support and adding nucleotides to the support. In forming the 42-base-pair DNA fragment, the first polynucleotide was provided with a length of twenty seven (27) nucleotides.

A second polynucleotide is formed in a similar manner with a second particular sequence of nucleotides such that the second polynucleotide is complementary to the first polynucleotide at the ends of the polynucleotides. Such ends may be the 3'-ends of the polynucleotides. In forming the 42-base-pair DNA fragment, the second polynucleotide was provided with a length of twenty five (25) nucleotides. The 3'-end of the second polynucleotide is complementary to the 3'-end of the first polynucleotide.

The 3'-ends of the polynucleotides are then hybridized or annealed to form a 10-base-pair complementary stretch. A repair synthesis is then provided in the first and second polynucleotides at the ends (such as the 5' ends) opposite the complementary stretch to provide a double-stranded polynucleotide. The repair synthesis may be monitored by labelling the 5'-ends of one or both of the nucleotides with radioactivity and then subjecting the nucleotides to an enzymatic reaction.

The method constituting this invention is disclosed in full detail in an article entitled "A Synthetic Consensus, Prokaryotic Promoter is Functional" by Xavier Soberon, John J. Rossi, Garrett Larson and Keiichi Itakura.

In the drawings:

FIG. 3 is a table of successive steps involved in preparing a resin support for the attachment of additional nucleotides to the resin support after the first nucleoside has been attached to the resin support;

Figure 7:
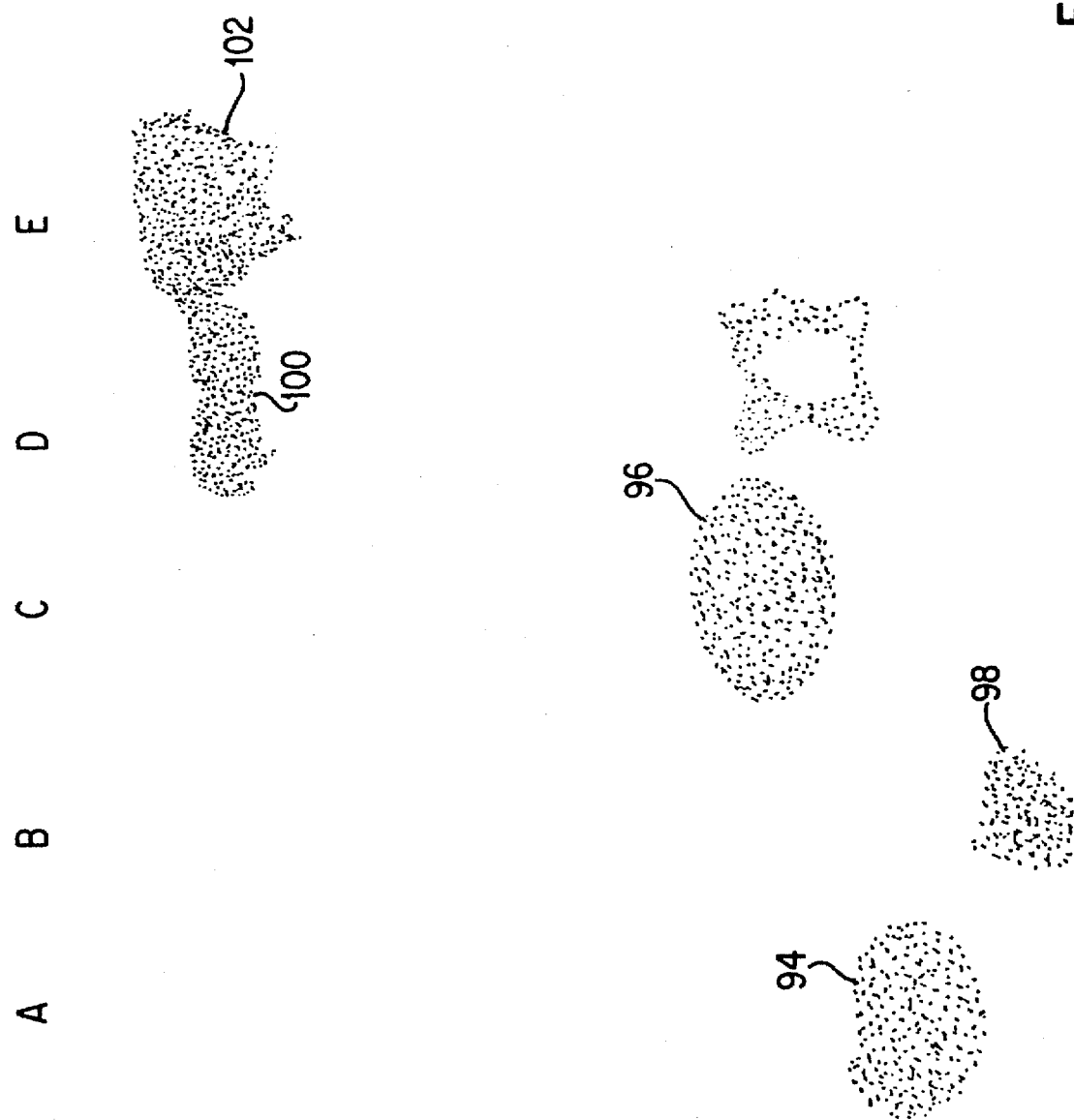

FIG. 7 constitutes an autoradiography of the two polynucleotides, the double stranded polynucleotide synthesized from such two polycleotides in the two alternative duplex structures shown in FIG. 5.

Figure 5A:
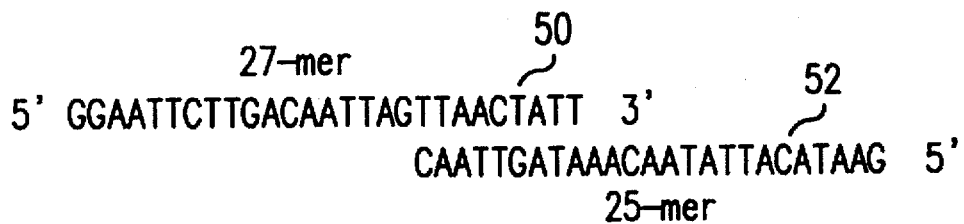
FIGS. 5A, 5B and 5C illustrate schematically the method in which a pair of polynucleotides are synthesized into a double-stranded polynucleotide of relatively long length and in which alternative duplex structures can possibly be formed.
Figure 5B:
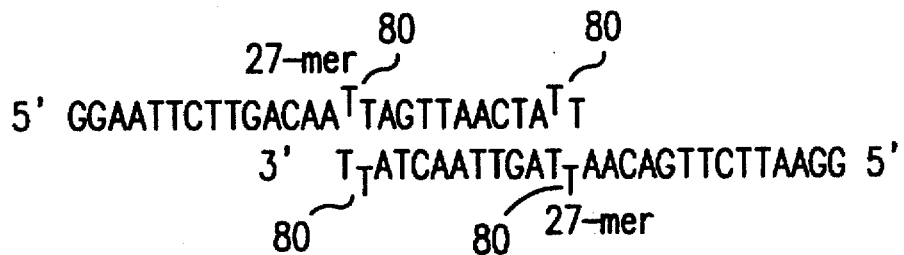
Figure 5C:
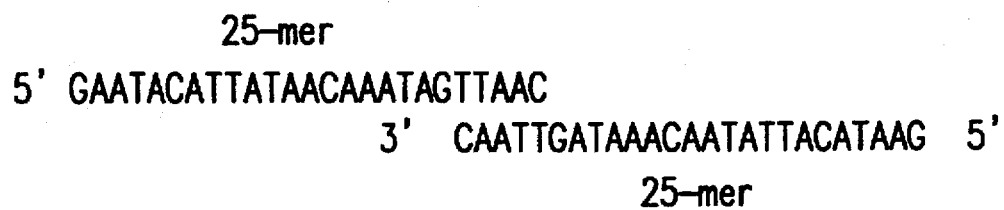
Figure 8A:
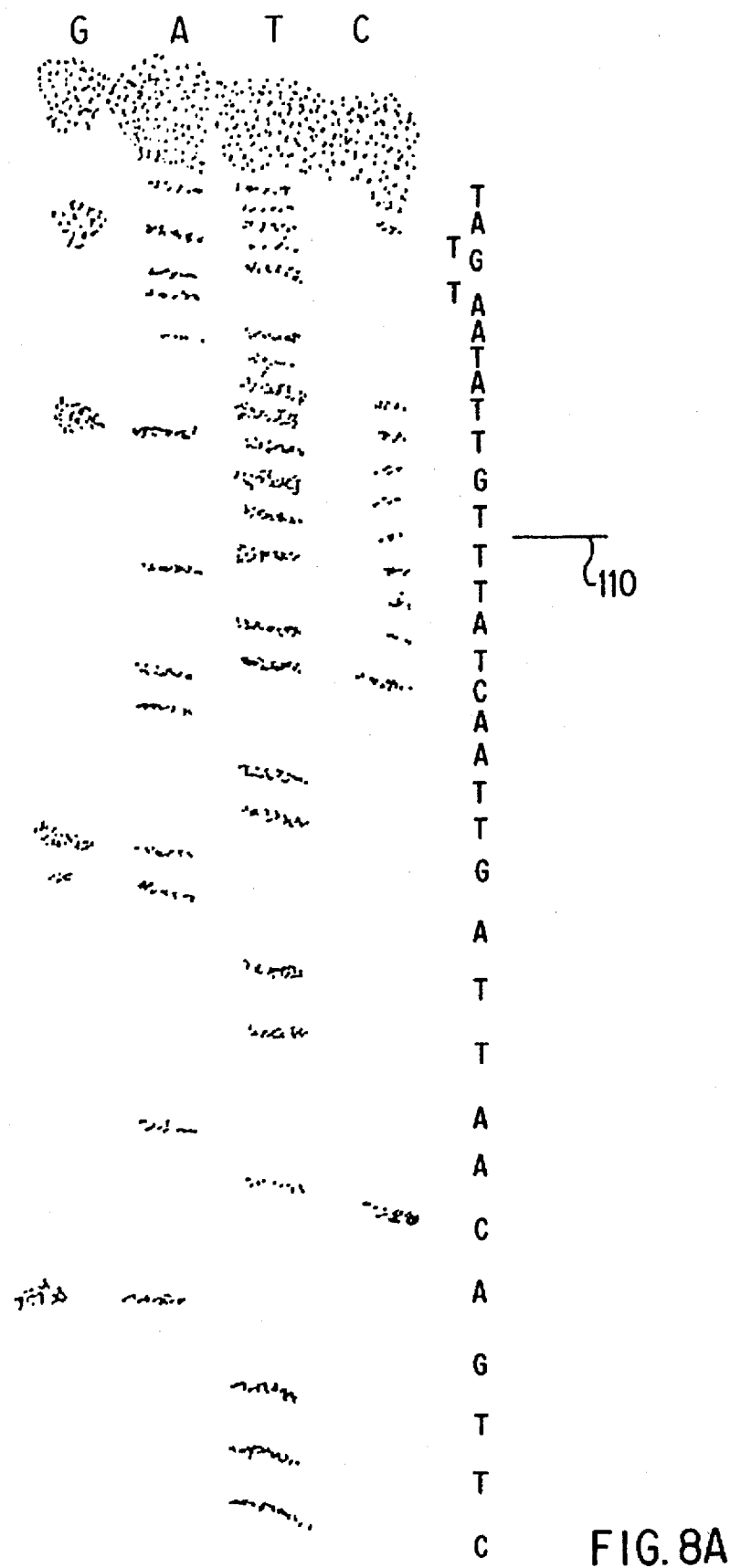
Figure 8B:
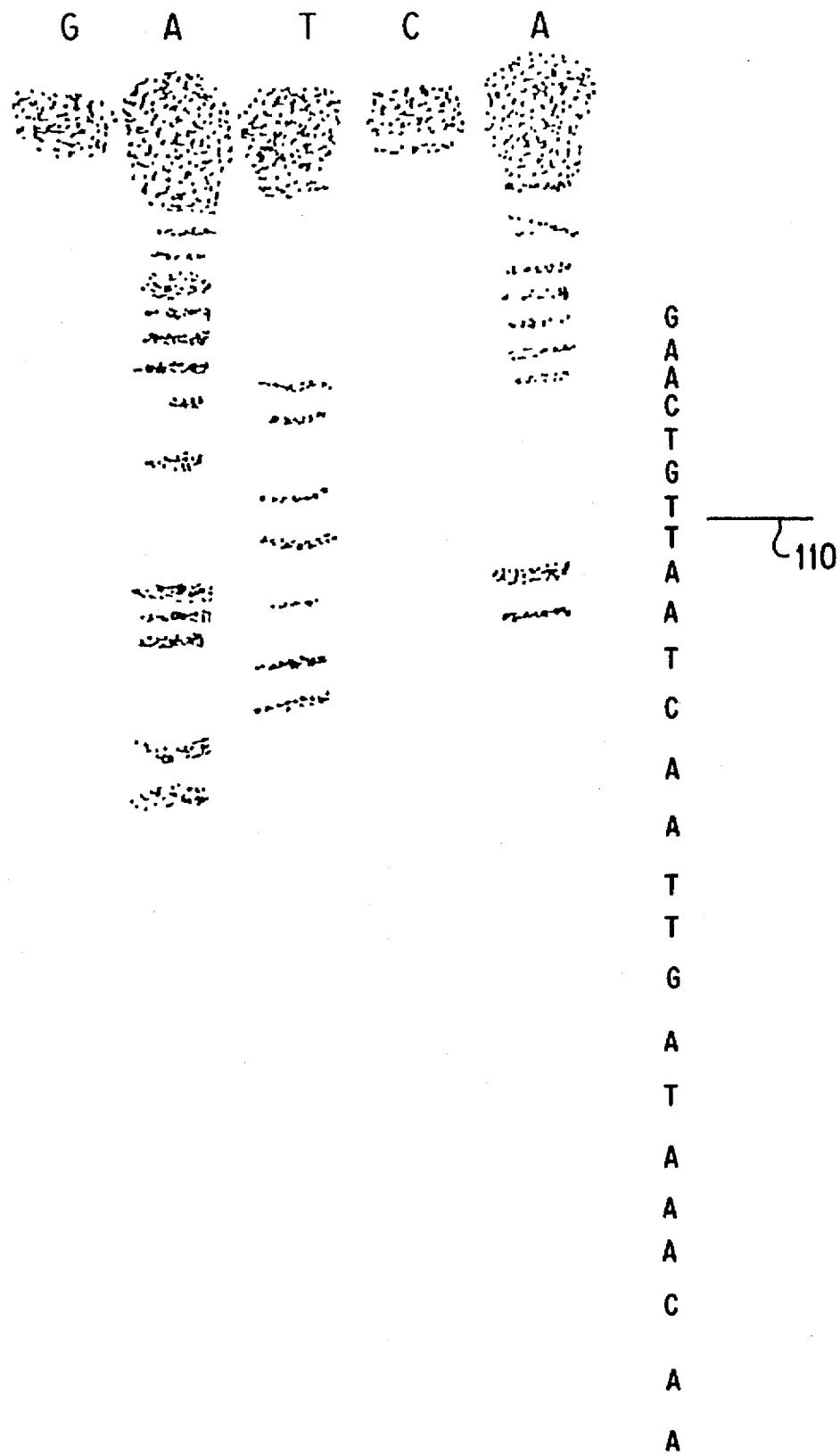
Figure 9:
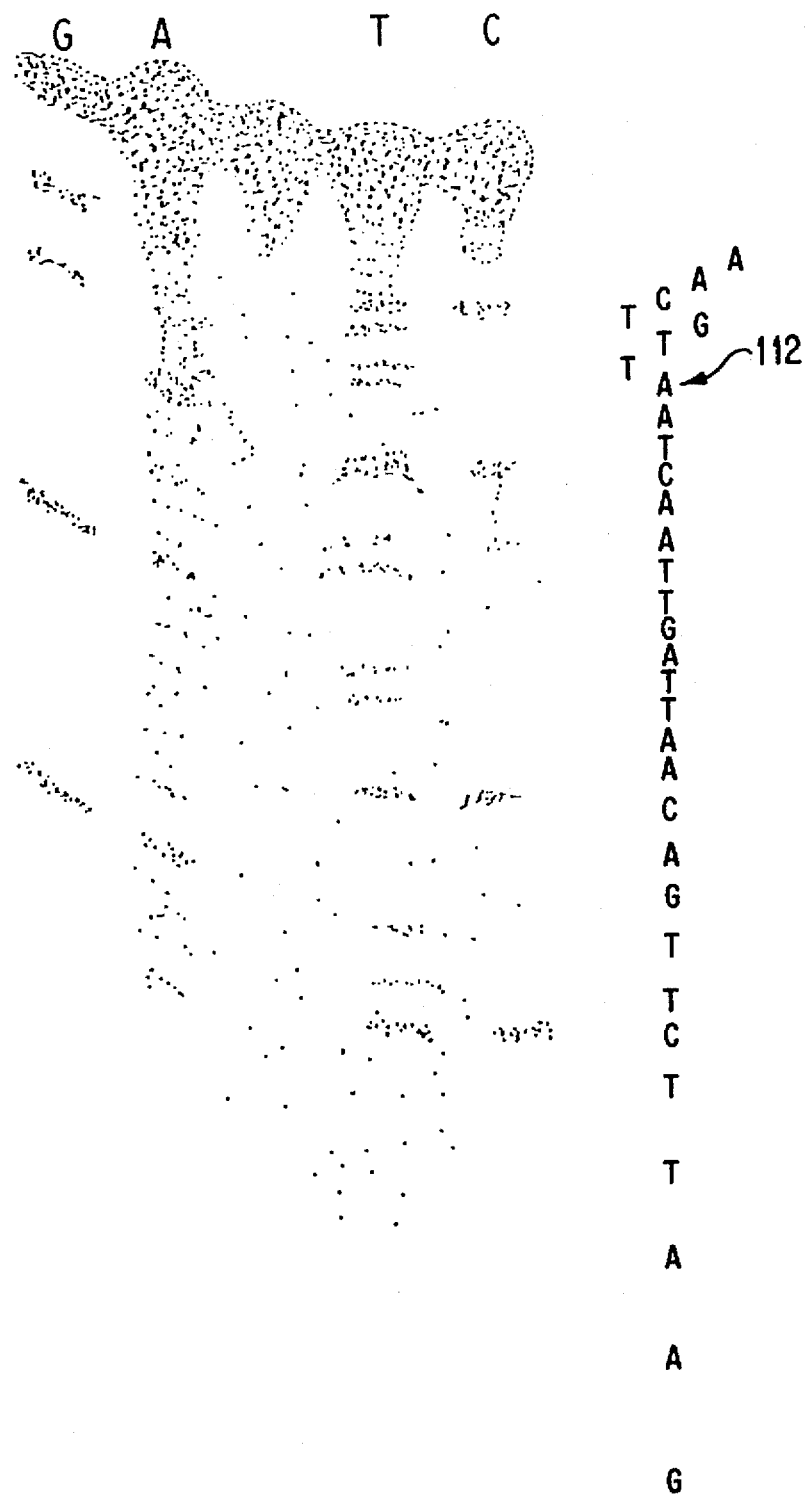

FIGS. 8A and 8B constitute autoradiographs of the different nucleotides in the two strands in the double-stranded polynucleotide synthesized by the method of this invention; and FIG. 9 constitutes autoradiographs of the different nucleotides in one of the two alternative structures shown in FIGS. 5B and 5C.

Figure 1:
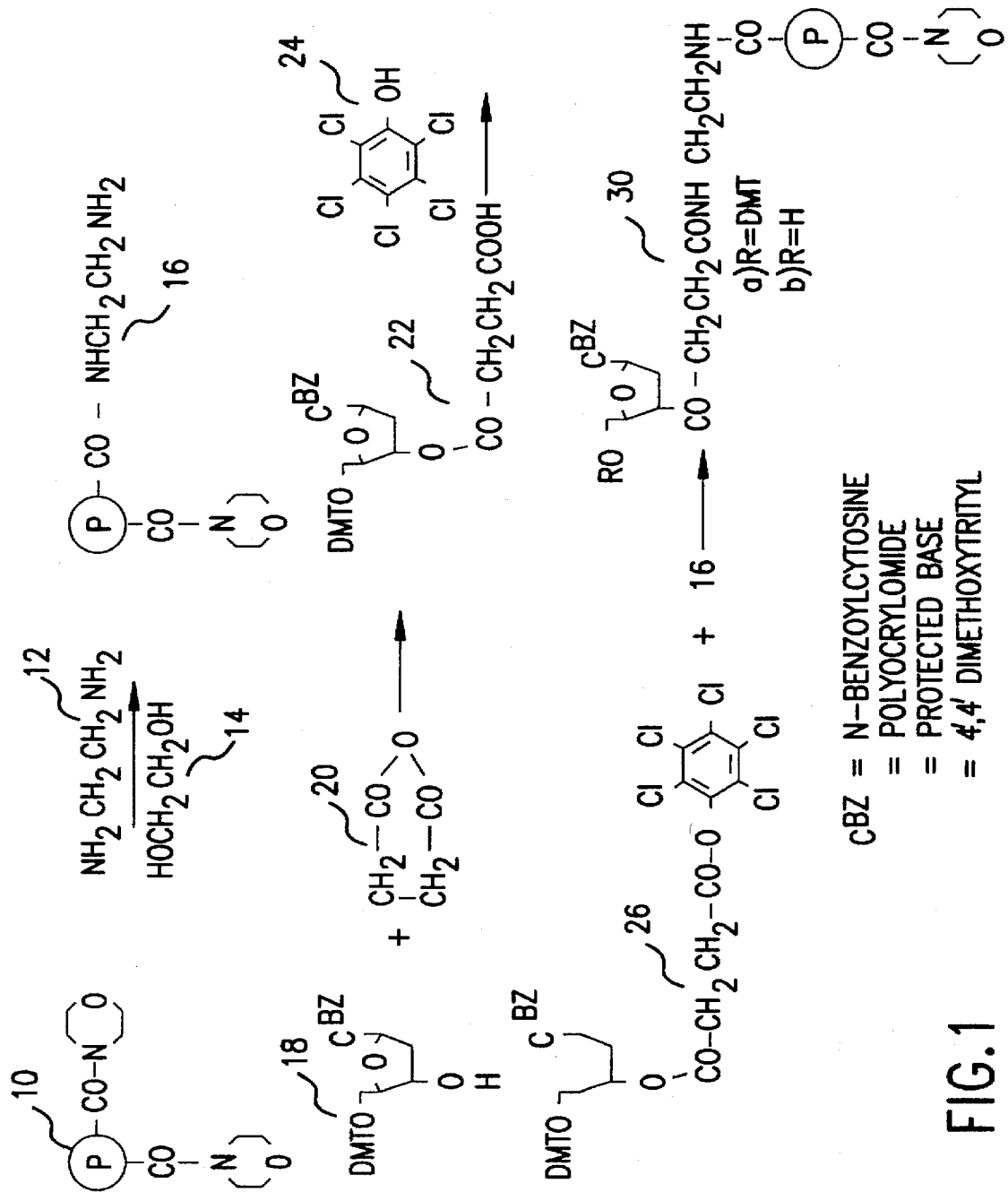
FIG. 1 illustrates the steps for providing a polyacrylmorpholide support and attaching a first nucleoside to such resin support.

In one embodiment of the invention, a polyacrylmorpholide resin 10 (FIG. 1) may be used as a solid-phase support for a polynucleotide. The polyacrylmorpholide resin 10 may be commercially available Enzacryl Gel K-2 resin marketed by the Aldrich Chemical Company. Such a commercially available resin may be derivatized with ethylenediamine 12 in ethylene glycol 14 to form an amino-resin 16 (0.20 mmole/g of the amino function).

A 5'-O-dimethoxytrityl deoxynucleoside 18 may be reacted with succinic anhydride 20 (1.5 mol equivalent) in the presence of a 4-(dimethylamino) pyridine (1.5 mol equivalent) in pyridine at a suitable temperature such as room temperature for an extended period such as overnight to provide a monosuccinate derivative 22 in a yield of approximately eighty percent (80%). The monosuccinate derivative 22 may be treated with pentachlorophenol 24 (1.1 mol equivalent) and dicyclohexylcarbodimide (3 mol equivalent) in dimethylformamide at a suitable temperature such as room temperature for an extended time such as approximately twenty (20) hours to form an activated ester 26 of the nucleoside in a yield of approximately ninety percent (90%).

The amino-resin 16 may be treated with the activated ester 26 of the nucleoside (2.5 mol equivalent) and triethylamine (2.75 mol equivalent) in dimethylformamide to provide an amino-bonded dimethoxytrityl resin 30. The formation of this resin may be facilitated by shaking the mixture at a suitable temperature such as room temperature for an extended period such as approximately twenty (20) hours.

Any unreacted amino group in the resin 30 may be masked by treatment with phenylisocyanate (10% solution in pyridine) at a suitable temperature such as room temperature for a suitable time such as approximately one (1) hour. The dimethoxytrityl group may then be removed by treatment with a two percent (2%) solution of benzenesulfonic acid 32 (FIG. 2) in $CHCl_3$-MeOH (7:3 v/v) at a suitable temperature such as room temperature for a relatively short time such as approximately thirty (30) seconds. In this way, a nucleoside 34 is obtained. The nucleoside serves as a support for the attachment of additional nucleotides by one of the methods of this invention to form a polynucleotide.

The method described above is disclosed in detail in the following article prepared by scientists who were employees of the assignee of record of this patent application at the time that such article was published:

"Solid-phase synthesis of hentriacontanucleotide" by Pietr Dembek, Ken-ichi Miyoshi and Keiichi Itakura. This article was published in Journal of the American Chemical Society in 1981 at Volume 103, pages 706–708.

FIG. 3 indicates the modifications of the removal condition of the dimethoxytrityl group from the nucleoside 34. The support may be initially washed with pyridine, as shown in step 1 of FIG. 3, and the 5'-hydroxyl group may then be masked with a ten percent (10%) solution of acetic anhydride, as shown in step 2 of FIG. 3. The resin support may then be washed with pyridine (Step 3 of FIG. 3) and may be subsequently washed a particular number of times (such as 3 times) with a $CHCl_3$-MeOH (7:3 v/v) solution which has been pre-cooled to a suitable temperature such as 0° C. This has been shown in Step 4 of FIG. 3. The dimethoxytrityl resin may be shaken with the pre-cooled solution of CHCl-MeOH to cool and swell the resin.

The resin support is then treated with a two percent (2%) solution of benzenesulfonic acid (BSA) in $CHCl_3$-MeOH (7:3 v/v, 10 ml). This treatment is shown in Steps 5 and 6 of FIG. 3. The treatment may occur for a suitable period of time such as approximately one (1) minute under a vigorous shaking. The nucleoside may then be washed in a suitable material such as pyridine. Such washing is illustrated in Steps 7 and 8 of FIG. 3. By this procedure, the dimethoxytrityl group is completely removed without harming the adenine residue in the oligonucleotide.

Figure 2:
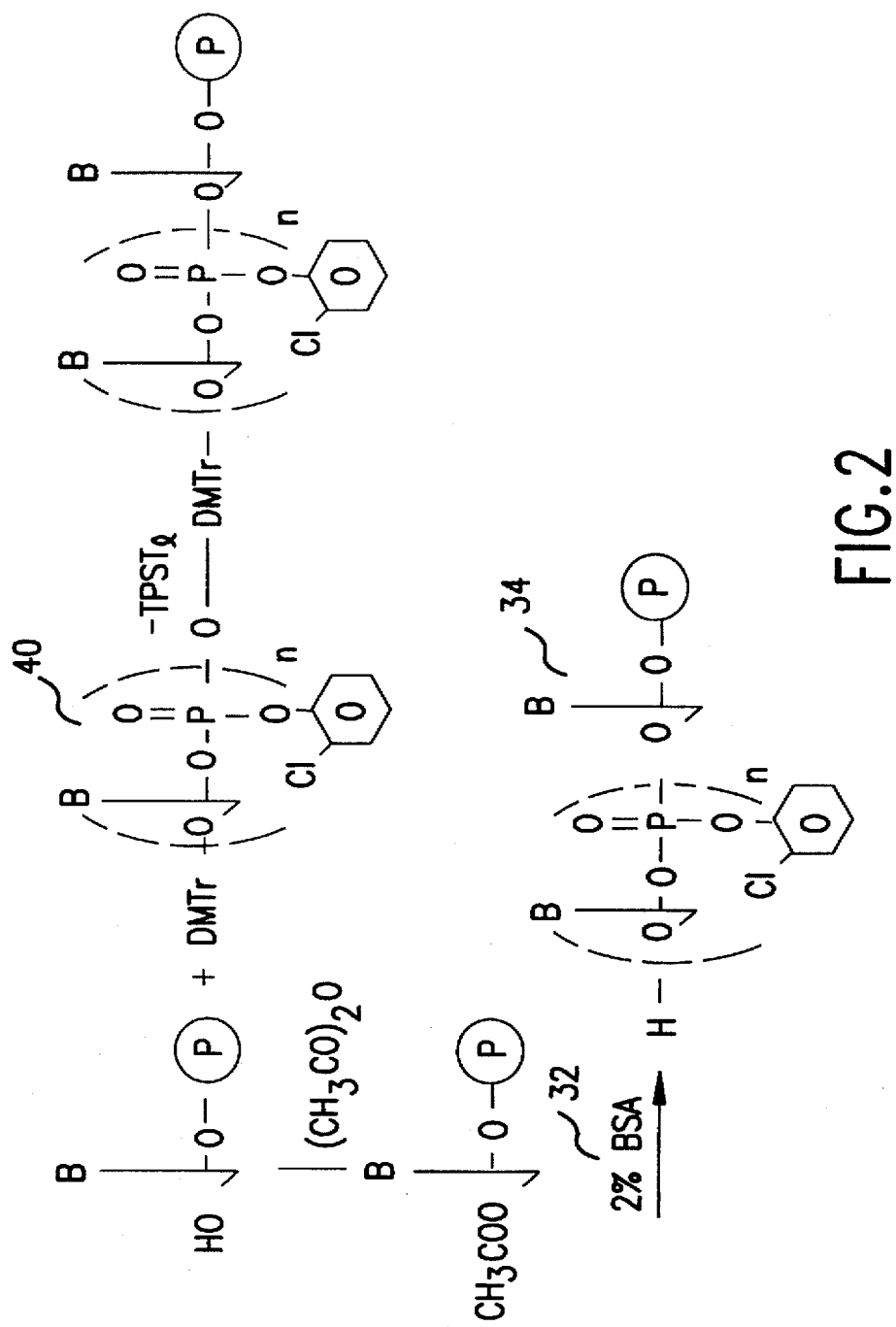
FIG. 2 illustrates the steps of adding mononucleotides, dinucleotides and trinucleotides to the resin support after the first nucleoside has been attached to the resin support the symbol n stands for the number of units enclosed by the broke line parenthesis.

Step 9 of FIG. 3 illustrates in a concise form the method of applicants for adding nucleotides to the resin support 30 to obtain a polynucleotide. In this step, "TPSTe" in FIG. 3 is intended to mean 2,4,6-triisopropylbenzenesulfonyl tetrazolide. In this step, the 2,4,6-triisopropylbenzenesulfonyl tetrazolide (15 mol equivalent) and anhydrous pyridine (8 ml) are added to the residue from Step 8 of FIG. 3 and the appropriate nucleotides to be coupled to the resin support are also added to the mixture. The reaction mixture is then shaken and filtered. This step is also shown in FIG. 2 wherein the appropriate nucleotide is designated at 40.

The methods described above and shown in FIGS. 1, 2 and 3 are disclosed in co-pending application Ser. No. 258,925 now U.S. Pat. No. 4,373,071 filed by Keiichi Itakura on Apr. 30, 1981, relating to "Solid-Phase Sythesis of Polynucleotides" and assigned of record to the assignee of record of this application. Alternative methods are also disclosed in application Ser. No. 258,925, now U.S. Pat. No. 4,373,071, and other methods are further disclosed in application Ser. No. 258,924, now U.S. Pat. No. 4,373,071, filed by Keiichi Itakura on Apr. 30, 1981, relating to "Solid-Phase Synthesis of Polynucleotides" and assigned of record to the assignee of record of this application.

In actual practice, two polynucleotides were formed by the methods described above and disclosed in application Ser. No. 285,925, now U.S. Pat. No. 4,373,071. One of these polynucleotides was formed with a sequence of twenty seven (27) nucleotides as illustrated at 50 in FIG. 5. A polyacrylmorpholide resin (500 mg), with the first nucleoside T (0.13 mmole/gram) at the 3'-end, was used for the polynucleotide 50. The dimer, trimer and tetramer blocks used (written in the 5' to 3' direction) to produce the polynucleotide 50 were as follows: AT, ACT, TTA, AG, AATT, GAC, CTT, ATT and GGA. These blocks were added in sequence, in nine (9) successive coupling cycles, to the nucleoside T bound to the polyacrylmorpholide resin. The average yield in the coupling cycles was approximately 78%.

The other of the polynucleotides was formed with a sequence of twenty five (25) nucleotides as illustrated at 52 in FIG. 5. A polyacrylmorpholide resin (500 mg), with the first nucleoside C (0.14 mmole/gram) at the 3'-end, was used for the polynucleotide 52. To produce the polynucleotide 52, the blocks AA, GTT, ATA, ACAA, ATA, ATT, TAC and GAA were sequentially added in eight (8) successive coupling cycles, to the nucleotide C bound to the polyacrylmorpholide resin. The average yield in the coupling cycles was approximately 76%.

In forming each of the polynucleotides 50 and 52, the yield of the coupling reaction did not decrease with the growing of the polynucleotide chain. This resulted from the use of a solid-phase support such as a polyacrylmorpholide. The efficient production of polynucleotides with long chains (or nucleotide sequences) by the use of solid-phase supports is in contrast to the difficulty in synthesizing, by a solution method, polynucleotides longer than an icosamer (a chain of 20 nucleotides) with a defined sequence. This difficulty occurs because there is no efficient method to isolate polynucleotides when a solution method is used.

Figure 4:
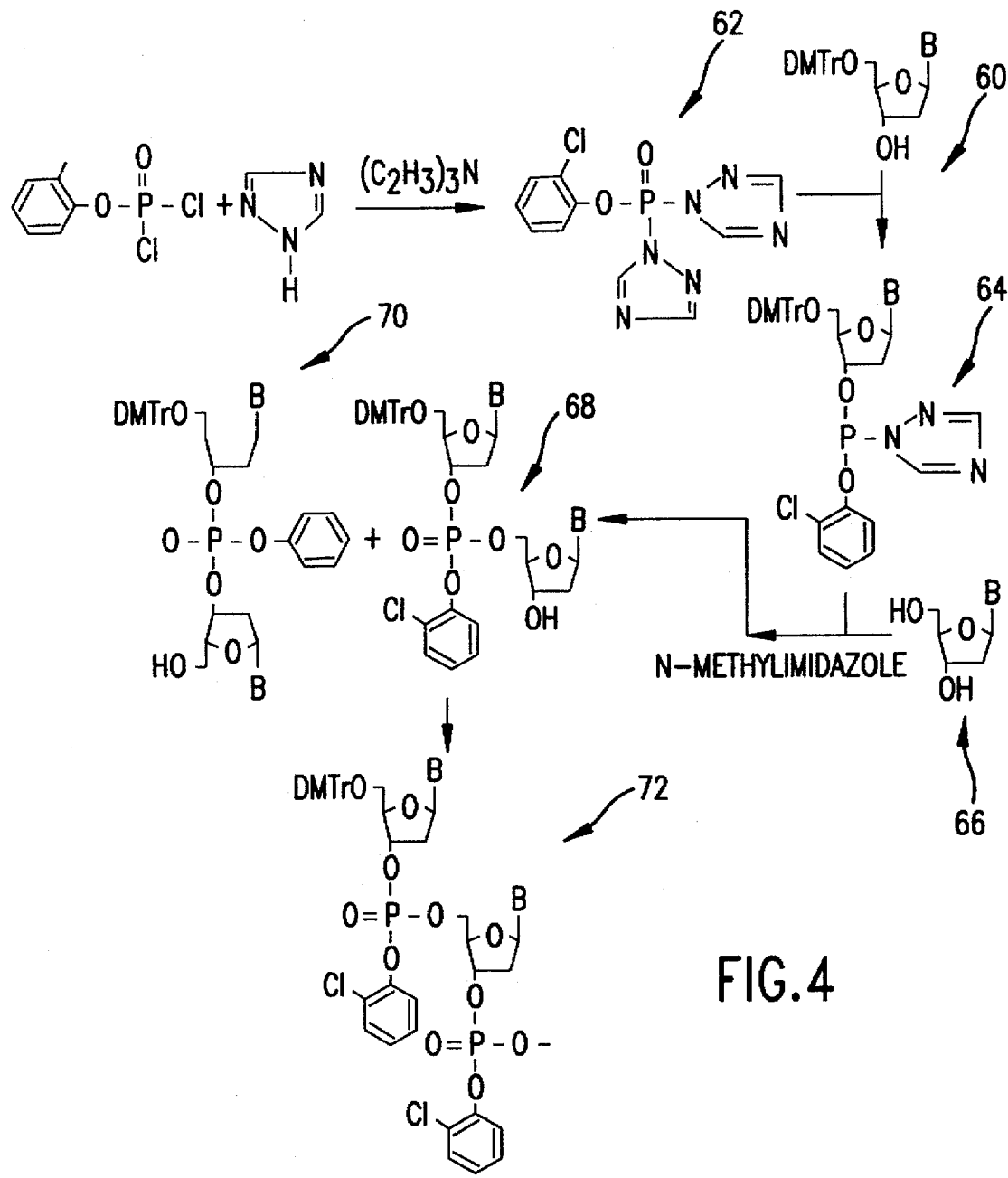
FIG. 4 illustrates the steps in an alternate method of adding dinucleotides to the resin support after the first nucleoside has been attached to the resin support.

Some of the dinucleotides used in this work were synthesized by an alternative method to that described above. The procedure is schematically presented in FIG. 4. 5'-dimethoxytrityl deoxynucleosides 60 (10 mmole) were phosphorylated with a ditriazolide 62 to produce the monotriazolide derivative 64. The dioxane solution of the monotriazolide derivative 64 was then added to 1.5 equivalents of an amino-protected 2'-deoxynucleoside 66, previously dried by repeated co-evaporation with pyridine. The reaction was performed in the presence of 5 equivalents of 1-methylimidazone as a nucleophilic catalyst. Under these conditions, the 5'-dimethoxytrityl dinucleotide 68 was obtained as the main product. The amount of by-products is variable, depending upon the sequence of the dimer prepared. One of those by-products is illustrated at 70.

The product 68 was purified by column chromatography on silica gel (10 g/mmole) using a stepwise gradient of methanol (0-5%) in chloroform. The procedure described was used only in those cases in which the difference between the main product 68 and the by-products (such as the 3'—3' dinucleotide 70) was large enough to make the chromatographic separation feasible and with a reasonable recovery.

Dinucleotides were phosphorylated in the same manner as the monomers with 2 equivalents of ditriazolide 62 and the resulting monotriazolides 64 hydrolyzed by the addition of aqueous pyridine (50%). The mixtures were evaporated, taken into chloroform and extracted with 0.2M triethylammonium bicarbonate (TEAB) buffer, pH7.5. The chloroform layer was collected, concentrated to a gum, dissolved in a small amount of pyridine or chloroform and added to a stirred mixture of ether-petroleum ether (1:1 v/v, 100 ml/mmol). The resulting precipitate was collected by centrifugation, washed with ether and the residual solvent immediately removed in vacuo. Dinucleotides 72 prepared in this manner have a charged phosphodiester at the 3' position and are stable for months at −20° C. in the desiccator. The yields of the final products were 40–60%.

As will be seen from FIG. 5A, the polynucleotides 50 and 52 have a 10-base-pair complementary stretch at a particular end such as their 3'-end. As further shown in FIG. 5A, the polynucleotides 50 and 52 are annealed or hybridized at their 3'-ends to form a 10-base-pair complementary stretch. A repair synthesis is then provided in the polynucleotides 50 and 52 at their opposite ends such as the 5'-ends. To facilitate this repair synthesis, the polynucleotides 50 and 52 are deblocked at the positions providing for the hybridization at the positions forming the complementary stretch and for the subsequent repair synthesis at their 5'-ends. Furthermore, to facilitate the hybridization or annealing of the polynucleotides 50 and 52 to form the complementary stretch and the repair synthesis of the polynucleotides, the polynucleotides should be purified after they have been deblocked.

The following procedure was used to deblock and purify the polynucleotides 50 and 52. A sample of the resin (10% of the total amount) was treated with 100 ul [1]M tetramethylguanidinium p-nitrobenzenealdoximate in dioxane-water (1:1 v/v) (10) and allowed to react for a suitable period of time such as 12–16 hours at a suitable temperature such as room temperature. 5 ul of tetramethylguanidine was added and the reaction continued for a suitable period of time such as 8 additional hours. To this mixture, 0.5 ml of pyridine and 2 ml of ammonium hydroxide were added and the tightly capped reaction tube shaken for an overnight period at a suitable temperature such as 50° C. The resin was filtered off and the solution evaporated to dryness and redissolved in 1 ml 0.01 M TEAB buffer, pH8. The whole sample was applied to a Sephadex G50–80 column (2.5×100 cm) and eluted with 0.01M triethylammonium bicarbonate (TEAB) buffer, pH8. The excluded material was collected, evaporated to dryness and redissolved in 500 ul of the same buffer. High performance liquid chromatography (HPLC) was performed using a uBondapak C18 column (Waters) on a SP3500 liquid chromatography (SpectraPhysics). The mixture was eluted by applying a linear acetonitrile gradient from 10–25% at pH7 (0.01M ethylenediammonium acetate buffer); the flow rate was 2 ml min with a sweep time of 20 minutes.

The fraction eluted at 8 minutes (FIG. 6) was collected, evaporated to dryness, redissolved in 1 ml 80% acetic acid in water and allowed to stand for 15 minutes at room temperature. The reaction mixture was concentrated, redissolved in 1 ml 0.1M TEAB buffer and extracted with ether three times. The sample was lyophilized twice and part of it ( 2.0 O.D. units) electrophoresed in a 20% polyacrylamide, 7M urea gel. Electro-elution of the DNA oligomers from the gel slices and their final purification over a BND cellulose column was performed as previously described with the exception that the column buffer contained 0.1M NaCl instead of 0.3M NaCl.

In many applications, ion exchange high performance liquid chromagraphs (HPLC) have been used on Permaphase AAX for the purification of the final reaction mixture to obtain a desired polynucleotide. However, the resolution of such chromagraph has been practically limited to polynucleotides smaller than an icosamer (a sequence of 20 nucleotides). To overcome this problem in obtaining each of the polynucleotides 50 and 52, reverse-phase HPLC was used to protect the partially deprotected polymers without removing the dimethoxytrityl (DMT) group.

As previously described, each of the coupling cycles involved the complete removal of the dimethoxytrityl group of the growing chain for the polynucleotides 50 and 52 prior to the addition of each new block to the chain and further involved the masking of unreacted 5'-hydroxyl groups after such complete removal. As a result, only the full-length polynucleotides 50 and 52 should contain the dimethoxytrityl (DMT) group. This should provide for the separation of the polynucleotide 50 from the mixture in which it is included. It should also provide for the separation of the polynucleotide 52 from the mixture in which it is included. Such a separation should occur because 5'-hydroxyl compounds are eluted faster on the reverse-phase column.

Figure 6B:
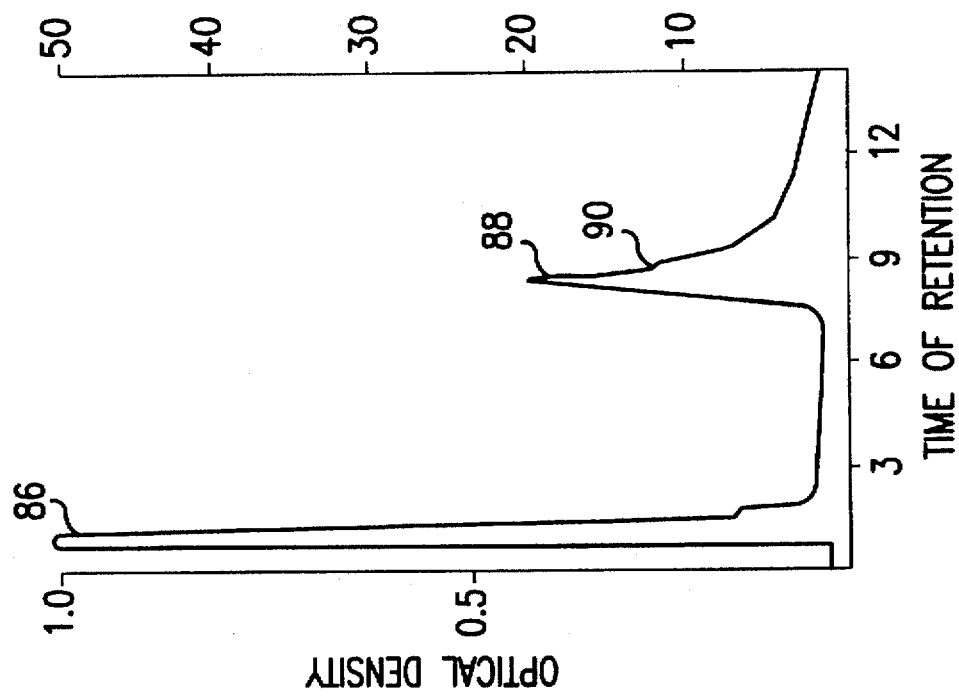
FIG. 6A and 6B illustrates high performance liquid chromagraphs (HPLC) of the two individual polynucleotides shown in FIG. 5.
Figure 6A:
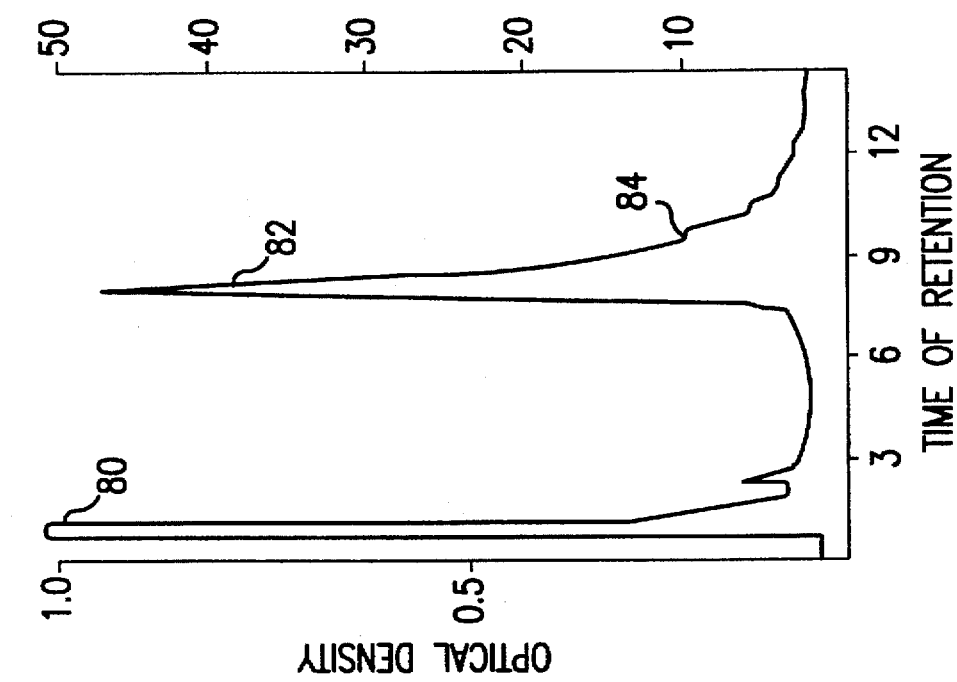

FIGS. 6A and 6B represent the high performance liquid chromagraphs respectively obtained from the mixtures containing the polynucleotides 50 and 52. As will be seen in FIG. 6A, the time of retention of the product is shown along the abscissa and the optical density (or ultra violet absorption) is shown along the ordinate. In FIG. 6A, a peak 80 is shown as being produced at an early time. This peak represents products which are relatively hydrophillic. Because of this, the products do not contain any dimethoxytrityl (DMT) groups. Another peak 82 is also produced at a relatively advanced time in the retention period. This peak represents the production of the polynucleotide 50, which has the dimethoxytrityl (DMT) group.

As will be seen, a shoulder 84 is produced adjacent the peak 82. This shoulder 84 represents the production of polynucleotides which are shorter in length than the chain of twenty-seven (27) nucleotides constituting the polynucleotide 50. These polynucleotides of shortened length contain the dimethoxytrityl (DMT) group. The production of such shortened polynucleotides could result from the incomplete removal of the dimethoxytrityl group during the synthesis and/or degradation produced in the deblocking operations.

In like manner, FIG. 6B represents the high performance liquid chromagraph for the polynucleotide 52. In this chromagraph, a peak 86 represents relatively hydrophillic products, thus containing no dimethoxytrityl (DMT) group. A peak 88 represents the polynucleotide 52 and a shoulder 90 adjacent the peak 88 represents shortened polynucleotides containing the dimethoxytrityl (DMT) group.

The material produced in the peak 82 in FIG. 6A was collected and analyzed by gel electrophoresis after removal of the dimethoxytrityl (DMT) group. This experiment showed that a major part of this peak had the desired length of nucleotides corresponding to the length of the polynucleotide 50, with a small percentage having a shortened length. Preparative gel electrophoresis was accordingly used for the final purificatio of the polynucleotides.

The polynucleotides 50 and 52 were then hybridized or annealed at their 3' ends at the positions to form the 10-basepair complementary stretch and a repair synthesis was provided at the 5'-ends of the polynucleotides by an enzymatic reaction. To accomplish this, the 5'-ends of the polynucleotides 50 and 52 were phosphorylated by using T4 polynucleotide kinase (Miles Labs) and were then labeled with [α-p$^{32}$]ATP. For the DNA polymerase reactions, appropriate amounts of each of the polynucleotides 50 and 52 (50 pmols for preparative procedures) were combined and the mixture brought to 40 μof 60 mM NaCl, 50 mM Tris.HCl pH7.6, 7mM Mg(OAc)$_2$, 7 mM DTT. The mixture was boiled for three minutes, chilled in ice and added to 10 μof a cocktail containing 5 mM of each deoxynucleotide triphosphate and 1–5 units DNA polymerase I (Klenow fragment, BoehringerMannheim) in the same buffer. The reaction was allowed to proceed at room temperature for 30 minutes. The product was phenol-extracted and ethanol-precipitated. Electrophoresis of the reaction products was performed on 10% acrylamide slab gels.

To obtain DNA sequencing, the DNA polymerase reactions were performed as above, with only one of the two fragments labeled. The double-stranded products were gel purified as described by J. J. Rossi, W. Ross, J. Egan, D. Lipman and A. Landy in Volume 128 of the Journal of Molecular Biology in 1979 at pages 21–47. The product was then subjected to each of the base-specific cleavage reactions described by Maxam and Gilbert in "Methods in Enzymology" (1980) at volume 65, pages 499–560. The partial cleavage products were resolved on slab gels (0.05× 20×50 cm), 12% polyacrylamide, 8M urea. Autoradiography was performed at –80° C. for 1–5 days with Kodak XRP-1 X-ray film and DuPont Cronex intensifying screens as described by Swanson and Shank in "Analytical Biochemistry" (1978) at volume 86, pages 184–192.

As previously described, the sequences of the polynucleotides 50 and 52 were designed to be hybridized or annealed so as to form a 10-base-pair complementary stretch along their 3'-ends. A reaction with E. coli DNA polymerase I (Klenow) caused the 5'-protruding ends of the polynucleotides 50 and 52 to be filled by respectively using the DNA fragments 50 and 52 as templates and primers for each other.

Besides the structure shown in FIG. 5A and described above, at least two additional double-stranded combinations (FIGS. 5B and 5C) could be expected to be formed in detectable amounts. One of these (FIG. 5B) would be formed by combinations of pairs of the polynucleotide 50 at their 3'-ends. The other of these would be formed by combinations of the pairs of the polynucleotides 52 at their 3'-ends.

The combination shown in FIG. 5B was actually formed. This combination occurred even though, at certain positions involving the base thymidine (T), the two polynucleotides 52 were not complementary. This is shown at 80 in FIG. 5B. It is represented by displacing the base (represented by the letter "T") vertically at these positions. The combination was able to be formed in spite of such absences of complementation at the positions 80 because the base thymidine is relatively weak, so that the repelling force at the positions 80 is relatively weak.

In order to favor the formation of the desired double-stranded product shown in FIG. 5A, a three (3)-fold molar excess of the polynucleotide 52 relative to the polynucleotide 50 was used and the DNA polymerase reaction was performed at room temperature. Under these conditions, the formation of the product shown in FIG. 5A should be preferred over the combinations shown in FIGS. 5B and 5C.

FIG. 7 shows an electrophoretic reaction on a polyacrylamide gel of the product of the DNA polymerase reactions with the combination of the polynucleotides 50 and 52. FIG. 7 also shows the products of the DNA polymerase reactions with each of the polynucleotides 50 and 52 above under the otherwise identical conditions.

As will be appreciated, the polynucleotides have negative charges. The polynucleotides are accordingly drawn to the positive pole which is represented as the bottom of FIG. 7. The distance moved is dependent upon the size of the polynucleotide. As a result, a polynucleotide with a relatively large chain of nucleotides moves through a shorter distance than a polynucleotide with a relatively short chain.

Column A of FIG. 7 represents the polynucleotide 52 and column C of FIG. 7 represents the polynucleotide 50. These polynucleotides move through relatively large distances and they appear in relatively great volume, as may be seen from the intensity of the indications 94 and 96 in columns A and C. Columns B and D provide indications 98 and 100 respectively representing the combinations of pairs of the polynucleotides 52 and pairs of the polynucleotides 50 when only the nucleotides 52 (column B) or 50 (column D) are present. The combinations of the pairs of the polynucleotides 52 in column B is relatively small, as may be seen from the slight intensity of the signal in column B. The combination of the pairs of the polynucleotides 50 in column D is greater than the combination of the pairs of the polynucleotides 52 but is still not as great as the intensities in columns A and C.

Column E provides an indication 102 representing the desired reaction to obtain the polynucleotide represented by the combination of the polynucleotides 50 and 52 shown in FIG. 5A. This reaction is relatively strong and efficient as shown by the intensity of the indication in column E. Since the desired product of the polymerase reaction (column E) differs in size by only two (2) base pairs from the reaction in column D, it was relatively difficult to estimate the relative proportions of the two (2) products by an inspection of the corresponding bands in a gel.

To obtain and monitor the nucleotide sequence of the 42-base-pair fragment shown in FIG. 5A, two (2) separate reactions with DNA polymerase were performed in which only one of the polynucleotides 50 and 52 was labelled at its 5'-end. The full-length polymerase products were purified by gel electrophoresis and their nucleotide sequences were obtained according to the procedure of Maxam and Gilbert in Volume 65 of the "Methods of Enzymology" at pages 499–560.

FIG. 8A illustrates the sequence obtained when the polynucleotide 50 was labelled. In FIG. 8A, the first band at the bottom of the radiogram is the C at position 7 of the polynucleotide 50 in the sequence from the 3'-end. The sequences of the first six (6) nucleotides were confirmed by additional experiments (data not shown).

Similarly, FIG. 8B shows a radiogram of the sequences obtained when the polynucleotide 52 was labelled. In FIG. 8B, the first band at the bottom of the sequence is the A at position 12 of the polynucleotide 52 from the 5'-end. The first eleven (11) positions in the sequence were confirmed by additional experiments (data not shown).

In FIGS. 8A and 8B, a line 110 is indicated. The positions above the line 110 in FIG. 8A represent the complement of the polynucleotide 52 at the free positions in FIG. 5A and the positions above this line in FIG. 8B represent the complement of the polynucleotide 50 at the free positions in FIG. 5A.

As will be seen in each of FIGS. 8A and 8B, a plurality of vertical columns is included. These columns respectively represent the G, A, T and C bases. The sequence of the nucleotides can accordingly be determined in FIGS. 8A and 8B by the indication in the particular one of the G, A, T and C columns for each of the different nucleotides positions indicated vertically at the right ends of these Figures.

FIG. 9 constitutes an autoradiogram of the nucleotide sequence when pairs of the polynucleotides 50 are combined in a DNA polymerase I reaction as illustrated in FIG. 5B. The first G detected in the gel at the bottom of FIG. 9 corresponds to position 1 from the 5'-end. As will be seen, a band unexpectedly appears in the A lane at position 26. This is indicated in FIG. 9 by an arrow and the numeral "112". Perhaps the simplest interpretation for this is that it constitutes a "correction" of the mismatched T (indicated at 80 in FIG. 5B) by the 3'-5' exonuclease activity of DNA polymerase I (Klenow fragment).

The invention accordingly provides a relatively simple and reliable method of producing polynucleotides having a relatively long sequence of nucleotides. The method involves the production of a pair of polynucleotides with complementary positions at first ends and the hybridization or annealing of the polynucleotides at their complementary positions and the provision of a repair synthesis in the polynucleotides at their opposite ends.

Although this application has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. A DNA polymerase mediated method for synthesizing a double stranded nucleic acid sequence which comprises (i) providing a first and second polynucleotide strands said first and second strands being initially unhybirdized to each other and each each initially having a 3' terminal sequence and an a adjoining 5"terminal sequence the 3' terminal sequences of said first and second strands being complementary to each other and having fewer nucleotides in length than either of the respective 5' terminal sequences each of said first and second strands said 3' terminal initial sequence of said first strand being a primer for a DNA polymerase mediated synthesis of an extension product complementary to the 5' terminal sequence of said second strand said initial 3' terminal sequence of said second strand being a primer for a DNA polymerase mediated synthesis of an extension product complementary to the 5' sequence of said first strand (ii) hybridizing the complementary 3' terminal portions of said initially unhybridized first and second strands and thereafter;

(iii) extending each of said hybridized 3' terminal end sequences to produce by in-vitro DNA polymerase mediated reaction an extension of said initial 3' terminal sequence of said first strand which is complementary to 5' portion of said second strand and extension of said 3' terminal sequence of said second strand which is complementary to cine 5' portion of said first strand.

2. A DNA polymerase mediated method for synthesizing a double stranded nucleic acid sequence which comprises (i) providing a first and a second single polynucleotide strand said first and second strands each being initially separate and unhybirdized to each other and each having a 3' terminal sequence and an 5' terminal sequence the 3' terminal sequences of said first and second stands being entirely complemtary to each other and having fewer nucleotides in length than either of the respective 5' terminal sequences in each of said first and second strands, said 3' terminal sequence of said first strand being a primer for a DNA polymerase mediated synthesis of an extension product complementary to the 5' sequence of said second strand said 3' terminal sequence of said second strand being a primer for a DNA polymerase mediated synthesis of an extension product complementary to the 5' sequence of said first strand (ii) hybridizing the complementary 3 terminal portions of said first and second strands (iii) extending each of said hybridized 3 terminal end sequences to produce by in-vitro DNA polymerase mediated reaction and an extension of said 3' terminal sequence of said first strand which is complementary to the 5' terminal portion of said second strand and an extension of said 3' terminal sequence of said second strand which is complementary to the 5' terminal portion of said first strand.

* * * * *

UNITED STATES PATENT AND TRADEMARK OFFICE
CERTIFICATE OF CORRECTION

PATENT NO.     : 5,750,380

DATED          : May 12, 1998

INVENTOR(S)    : Keiichi ITAKURA et al.

It is certified that error appears in the above-identified patent and that said Letters Patent is hereby corrected as shown below:

After the title insert the following:

--This invention was made with government support in the form of Grant No. GM 26408 and Grant No. GM 30395 from the National Institutes of Health. The government may have certain rights in the invention.--

Signed and Sealed this

Twenty-third Day of February, 1999

Attest:

Q. TODD DICKINSON

*Attesting Officer*     *Acting Commissioner of Patents and Trademarks*